United States Patent [19]

Williams

[11] Patent Number: 5,272,344
[45] Date of Patent: Dec. 21, 1993

[54] AUTOMATED COINCIDENCE TIMING CALIBRATION FOR A PET SCANNER

[75] Inventor: John J. Williams, Hartland, Wis.

[73] Assignee: General Electric Company, Milwaukee, Wis.

[21] Appl. No.: 974,642

[22] Filed: Nov. 10, 1992

[51] Int. Cl.⁵ .................. G01T 1/161; G01T 1/17; A61B 6/00; G01T 1/17

[52] U.S. Cl. .................. 250/363.03; 250/252.1

[58] Field of Search .................. 250/252.1 A, 252.1 R, 250/363.03, 363.04, 363.09, 369

[56] References Cited

FOREIGN PATENT DOCUMENTS

| | | | |
|---|---|---|---|
| 59-35170 | 2/1984 | Japan | 250/363.03 |
| 59-99377 | 6/1984 | Japan | 250/363.03 |
| 61-132888 | 6/1986 | Japan | 250/363.03 |

Primary Examiner—Constantine Hannaher
Assistant Examiner—Edward J. Glick
Attorney, Agent, or Firm—Quarles & Brady

[57] ABSTRACT

A PET scanner operates in a calibration mode to produce timing calibration sinograms. These sinograms are employed to calculate time delay adjustment values for each detector channel. These values are downloaded to data acquisition circuits in each detector channel to adjust the delay of event data pulses that indicate the occurrence of a coincidence event. The process is repeated until the downloaded time delay values are reduced below preset criteria.

8 Claims, 4 Drawing Sheets

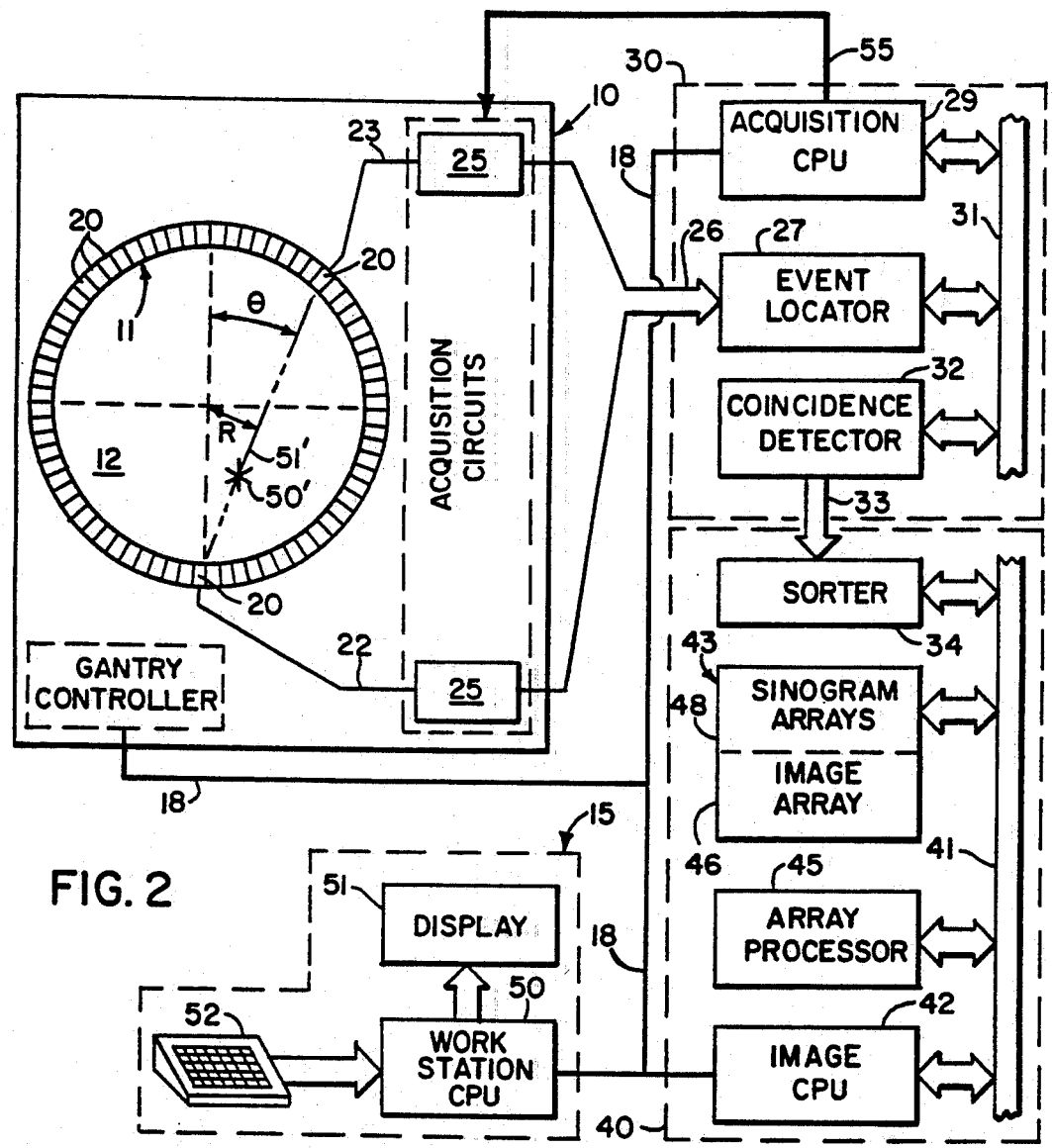

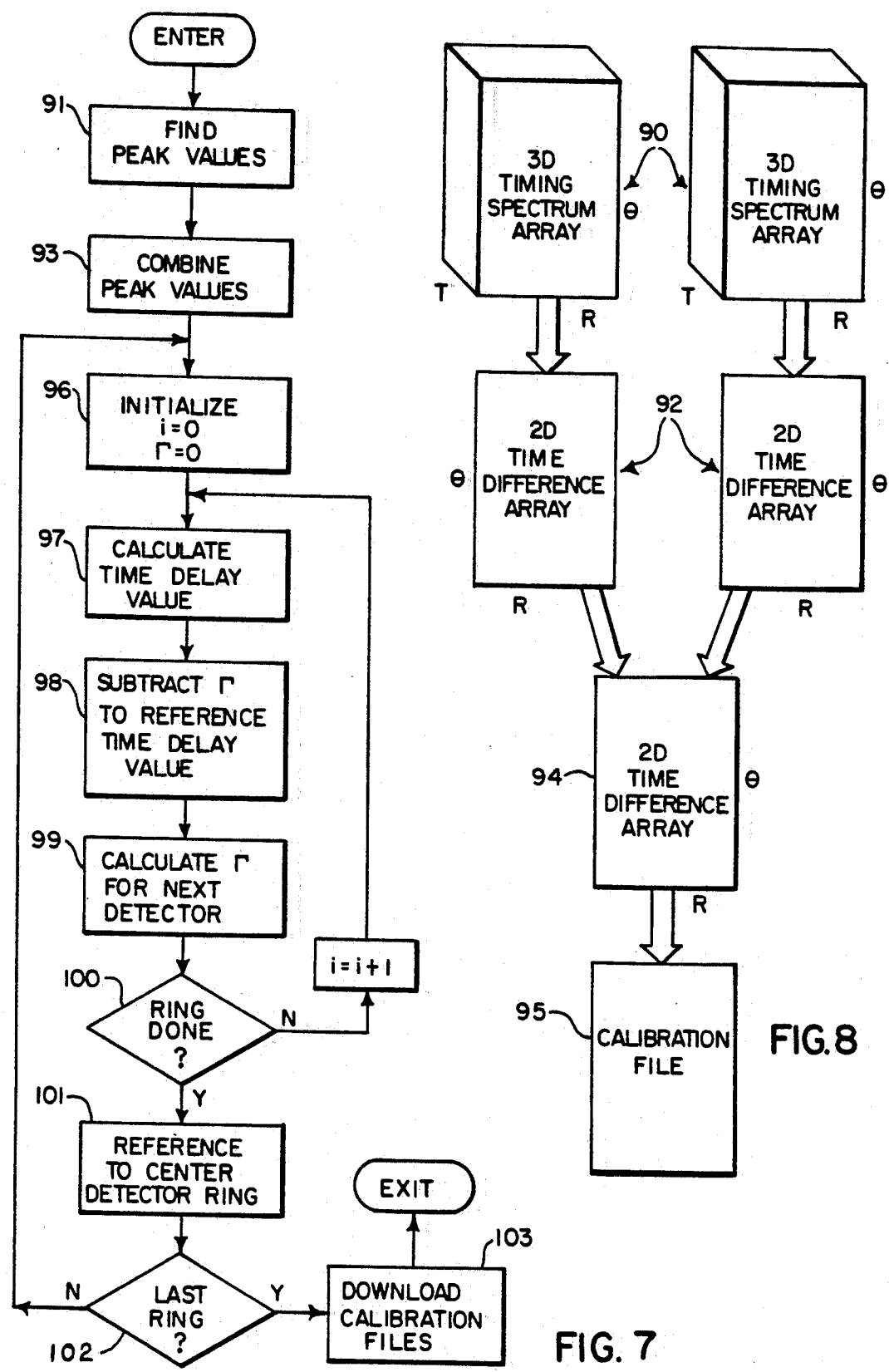

AUTOMATED COINCIDENCE TIMING CALIBRATION FOR A PET SCANNER

BACKGROUND OF THE INVENTION

The field of the invention is positron emission tomography (PET) scanners, and particularly the calibration of such scanners.

Positrons are antimatter electrons which are emitted by radionuclides that have been prepared using a cyclotron or other device. The radionuclides commonly employed in diagnostic imaging are fluorine-18 ($^{18}$F), carbon-11 ($^{11}$C), nitrogen-13 ($^{13}$N), and oxygen-15 ($^{15}$O). These are employed as radioactive tracers called "radiopharmaceuticals" by incorporating them into substances, such as glucose or carbon dioxide. The radiopharmaceuticals are injected in the patient and become involved in such processes as glucose metabolism, fatty acid metabolism and protein synthesis.

As the radionuclides decay, they emit positrons. The positrons travel a very short distance before they encounter an electron, and when this occurs, a matter-antimatter annihilation converts them into two photons, or gamma rays. This annihilation event is characterized by two features which are pertinent to PET scanners— each gamma ray has an energy of 511 keV and the two gamma rays are directed in substantially opposite directions. An image is created by determining the number of such annihilation events at each location within the field of view.

The PET scanner includes one or more rings of detectors which encircle the patient and which convert the energy of each 511 keV photon into a flash of light that is sensed by a photomultiplier tube (PMT). Coincidence detection circuits connect to the detectors and record only those photons which are detected simultaneously by two detectors located on opposite sides of the patient. The number of such simultaneous events indicates the number of positron annihilations that occurred along a line joining the two opposing detectors. Within a few minutes millions of events are recorded to indicate the number of annihilations along lines joining pairs of detectors in the ring. These numbers are employed to reconstruct an image using well known computed tomography techniques.

One of the vital calibration operations in a PET scanner is the coincidence timing calibration. The purpose of this calibration is to correct for relative timing differences in the detection modules and the "front end" electronics of the PET scanner. This calibration is traditionally performed by placing a source of positrons at the center of the detector rings and adjusting each channel of the front end electronics manually until the coincident events registered by each channel is maximized and relatively uniform around the entire ring. This is a time consuming iterative process in which many manual adjustments are made and long data collection times are required.

More recently, a PET scanner has been proposed in which the time difference between the signals which record coincidence events can be maintained by the scanner. Since the photons travel an equal distance to the two detectors which record a coincidence event, their signals should indicate an event at precisely the same moment. Any difference in time, therefore, represents an error caused by differences in the detectors, PMTs or electronic circuits. As described in co-pending U.S. application Ser. No. 920,350 entitled "Sorter For Coincidence Timing Calibration In A PET Scanner," the time difference information may be gathered and stored as a sinogram calibration array when the PET scanner is operated in a calibration mode. These time differences can be offset by introducing appropriate delays in the scanner's front end electronics.

SUMMARY OF THE INVENTION

The present invention is a method for automatically adjusting the front end electronics in a PET scanner to reduce timing errors. More specifically, the method includes: producing timing data which indicates the measured time differences of coincidence events occurring between each pair of detectors lying within the field of view of the PET scanner; calculating an incremental time delay for a detector in the ring by averaging the time difference values in the timing data which corresponds with pairs of detectors lying within the field of view of the PET scanner as seen from the detector; calculating a reference correction which relates the incremental time delay to the time delay calculated for a detector designated as the reference; combining the incremental time delay with the reference correction to produce the time delay adjustment value for the detector; repeating these steps for successive detectors in the ring until time delay values have been produced for all detectors in the ring; and downloading the time delay values to the corresponding detector channels in the front end electronics to effect their timing.

A general object of the invention is to automatically adjust the time delay in each detector channel. The calibration timing array is obtained by placing the PET scanner in calibration mode and acquiring coincidence timing data using an orbiting reference source of positrons. A calibration data file is calculated from the calibration timing data and this is downloaded to the front end electronics to adjust the time delay in each detector channel such that the time differences between channels is calculated to be zero. Because of the absolute accuracy of the timing adjustments, a scattering of residual timing errors will remain and the process may be repeated a number of times until the measured time differences in the sinogram calibration data file reaches a minimal amount. Three or four iterations have been found sufficient to drive the timing errors down to the resolution of a single increment of timing adjustment.

A more specific object of the invention is to provide a method and means for calculating a downloadable calibration file from a sinogram calibration time difference data array.

A general object of the invention is to quickly and accurately calibrate the timing of each detector channel in a PET scanner. When switched to the timing calibration mode, the system simultaneously acquires timing data for each detector pair and stores it in a three-dimensional array. This timing data is converted by calculation to a calibration file containing a time delay value for each detector channel. The calibration file is downloaded and the time delays in each detector channel are changed accordingly. The process may be repeated until the time delay values in the calibration file are reduced to specified values which insure highly accurate coincidence timing of all detector channels.

A more specific object of the invention is to efficiently calculate time delay values from coincidence timing data. The time delay value for each detector channel is calculated by averaging timing data for rays within the field of view of the PET scanner as seen from the detector. This timing value is adjusted to reference it to the adjacent detector element by calculating a reference correction value in which timing data for rays in the same field of view as seen from the adjacent detector are averaged. The process continues around the detector ring until timing values and reference corrections have been calculated for all the detector channels.

The foregoing and other objects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims herein for interpreting the scope of the invention.

BRIEF DESCRIPTION OF THE DRAWINGS

FIG. 2 is a schematic diagram of the PET scanner system of FIG. 1;

FIG. 3 is a pictorial view of a detector module which forms part of the PET scanner system of FIG. 1;

FIG. 7 is a flow chart of the program executed by the PET scanner system of FIG. 2 to carry out the timing calibration of the present invention;

FIG. 8 is a schematic representation of the data structures employed by the program of FIG. 7.

DESCRIPTION OF THE PREFERRED EMBODIMENT

Figure 1:
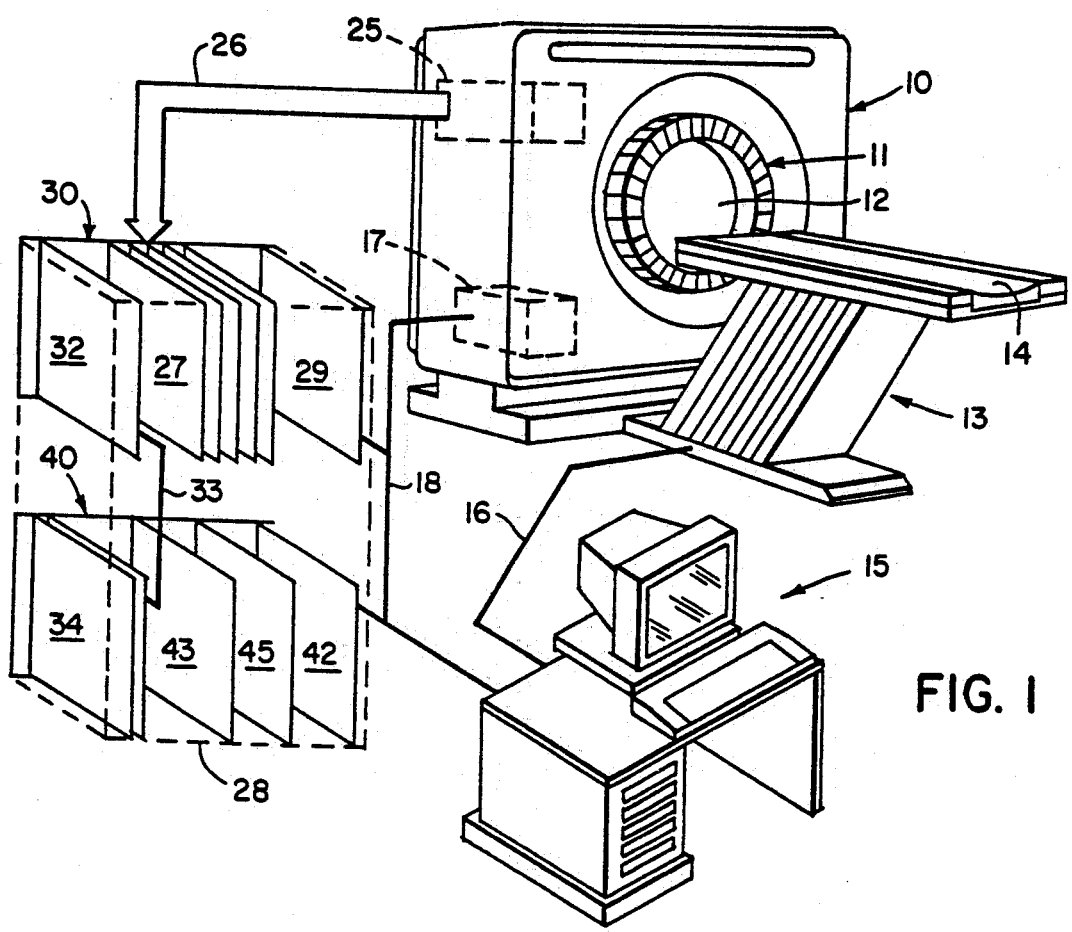
FIG. 1 is a pictorial view with parts cut away of a PET scanner system which employs the present invention.

Referring particularly to FIG. 1, the PET scanner system includes a gantry 10 which supports a detector ring assembly 11 about a central opening, or bore 12. A patient table 13 is positioned in front of the gantry 10 and is aligned with the central axis of the bore 12. A patient table controller (not shown) moves the table bed 14 into the bore 12 in response to commands received from an operator work station 15 through a serial communications link 16. A gantry controller 17 is mounted within the gantry 10 and is responsive to commands received from the operator work station 15 through a second serial communication link 18 to operate the gantry. For example, the gantry can be tilted away from vertical on command from the operator, it can perform a "transmission scan" with a calibrated radionuclide source to acquire attenuation measurements, it can perform a "coincidence timing calibration scan" to acquire corrective data, or it can perform a normal "emission scan" in which positron annihilation events are counted.

As shown best in FIGS. 2 and 3, the detector ring 11 is comprised of 112 detector channels 20. Each detector channels 20 includes a set of thirty-six bismuth germinate scintillator crystals 21 (abbreviated BGO) arranged in a 6×6 matrix and disposed in front of four photomultiplier tubes 22 (abbreviated PMT). Each PMT 22 produces an analog signal 23A–23D which rises sharply when a scintillation event occurs then tails off exponentially with a time constant of 300 nanoseconds. The relative magnitudes of the analog signals 23A–23D is determined by the position in the 6×6 BGO matrix at which the scintillation event took place, and the total magnitude of these signals is determined by the energy of the gamma ray which caused the event.

A set of acquisition circuits 25 are mounted within the gantry 10 to receive the four signals 23A–23D from each of the detector channels 20 in the detector ring 11. The acquisition circuits 25 determine the event coordinates within the block of BGO crystals 21 by comparing the relative signal strengths as follows:

$$x = (A+C)/(A+B+C+D); \quad (1)$$

$$z = (A+B)/(A+B+C+D). \quad (2)$$

These coordinates (x,z), along with the sum of all four signals (A+B+C+D) are then digitized and sent through a cable 26 to an event locater circuit 27 housed in a separate cabinet 28. Each acquisition circuit 25 also produces an event detection pulse (EDP) which indicates the exact moment the scintillation event took place.

The timing errors which are the subject of the present invention originate in the above described front end electronics of the PET scanner. Timing differences between each channel arise because of variations in the BGO crystals, variations in PMT delays, variations in the analog circuitry and variations in the lengths of the conductive paths. The timing corrections made by the present invention are measured in picoseconds. As will be described in more detail below, these timing corrections change the arrival times of the EDP pulses at the event locater circuit 27 where the timing is digitized.

Referring particularly to FIGS. 1 and 2, the event locater circuits 27 form part of a data acquisition processor 30 which periodically samples the signals produced by the acquisition circuits 25. The processor 30 has a backplane bus structure 31, and an acquisition CPU 29 controls communications on this bus 31 and links the processor 30 to the local area network 18. The event locator 27 is comprised of a set of separate circuit boards which each connect to the cable 26 and receive signals from corresponding acquisition circuits 25 in the gantry 10. The event locator 27 synchronizes the event with the operation of the processor 30 by detecting the event pulse (EDP) produced by an acquisition circuit 25, and converting it into an 8-bit time marker which indicates when within the current 250 nanosecond sample period the scintillation event took place. Also, this circuit 27 discards any detected events if the total energy of the scintillation is outside the range of 511 keV±20%. During each 250 nanosecond sample period, the information regarding each valid event is assembled into a set of digital numbers that indicate precisely when the event took place and the position of the BGO crystal 21 which detected the event. This event data packet is conveyed to a coincidence detector 32 which is also part of the data acquisition processor 30.

The coincidence detector 32 accepts the event data packets from the event locators 27 and determines if any two of them are in coincidence. Coincidence is determined by a number of factors. First, the time markers in each event data packet must be within 12.5 nanoseconds of each other, and second, the locations indicated by the two event data packets must lie on a straight line which passes through the field of view (FOV) in the scanner bore 12. Events which cannot be paired are discarded, but coincident event pairs are located and recorded as a coincidence data packet that is conveyed through a serial link 33 to a sorter 34. Each coincidence data packet includes a pair of digital numbers which precisely identify the addresses of the two BGO crystals 21 that detected the event. For a more detailed description of the coincidence detector 32, reference is made to co-pending U.S. patent application Ser. No. 919,456 filed on Jul. 27, 1992, and is entitled "Coincidence Detector For A PET Scanner" and which is incorporated herein by reference.

The sorter 34 is a circuit which forms part of an image reconstruction processor 40. The image reconstruction processor 40 is formed about a backplane bus 41. An image CPU 42 controls the backplane bus 41 and it links the processor 40 to the local area network 18. A memory module 43 also connects to the backplane 41 and it stores the data used to reconstruct images as will be described in more detail below. An array processor 45 also connects to the backplane 41 and it operates under the direction of the image CPU 42 to perform the image reconstruction using the data in memory module 43. The resulting image array 46 is stored in memory module 43 and is output by the image CPU 42 to the operator work station 15.

The function of the sorter 34 is to receive the coincidence data packets and generate from them memory addresses for the efficient storage of the coincidence data. The set of all projection rays that point in the same direction ($\theta$) and pass through the scanner's field of view is a complete projection, or "view". The distance (R) between a particular projection ray and the center of the field of view locates that projection ray within the view. As shown in FIG. 2, for example, an event 50' occurs along a projection ray 51' which is located in a view at the projection angle $\theta$ and the distance R. The sorter 34 counts all of the events that occur on this projection ray (R,$\theta$) during the scan by sorting out the coincidence data packets that indicate an event at the two BGO detector crystals lying on this projection ray. During an emission scan, the coincidence counts are organized in memory 43 as a set of two-dimensional arrays, one for each axial image, and each having as one of its dimensions the projection angle $\theta$ and the other dimension the distance R. This $\theta$ by R map of the measured events is called a histrogram, or more commonly the sinogram array 48.

Coincidence events occur at random and the sorter 34 quickly determines the $\theta$ and R values from the two crystal addresses in each coincidence data packet and increments the count of the corresponding sinogram array element. The values of $\theta$ and R may be calculated as follows, although in the preferred embodiment these are converted to memory addresses.

$$\theta = (\phi_2 + \phi_1)/2 + 90° \quad (3)$$

$$R = (r_0 \cos[(\phi_2 - \phi_1)/2] \quad (4)$$

where
$\phi_1$ = angular orientation of first detector crystal;
$\phi_2$ = angular orientation of second detector crystal; and
$r_0$ = radius of detector ring.

At the completion of the emission scan, the sinogram array 48 stores the total number of annihilation events which occurred along each ray (R,$\theta$). In the preferred embodiment, there are three rings of detector channels and sinogram arrays 48 are acquired for each ring during a scan. In addition, coincidence events which occur across adjacent detector rings are also recorded and a pair of sinogram arrays 48 are formed for coincidence events occurring between the center detector ring and each of the outer detector rings. A total of seven sinogram arrays 48 are thus available from which multiple slice images or three-dimensional images can be reconstructed.

The array processor 45 reconstructs an image from the data in the sinogram array 48. First, however, a number of corrections are made to the acquired data to correct for measurement errors such as those caused by attenuation of the gamma rays by the patient, detector gain nonuniformities, random coincidences, and integrator deadtime. Each row of the corrected sinogram array is then Fourier transformed by the array processor 45 and multiplied by a one-dimensional filter array. The filtered data is then inverse Fourier transformed, and each array element is backprojected to form the image array 46. The image CPU 42 may either store the image array data on disk or tape (not shown) or output it to the operator work station 15.

The operator work station 15 includes a CPU 50, a CRT display 51 and a keyboard 52. The CPU 50 connects to the local area network 18 and it scans the key board 52 for input information. Through the keyboard 52 and associated control panel switches, the operator can control the calibration of the PET scanner, its configuration, and the positioning of the patient table for a scan. For example, the operator can download to the sorter 34 through the local area network 18 configuration data and data which indicates whether the scanner is performing an emission scan, an attenuation scan, or a coincidence calibration timing scan. Similarly, the operator can control the display of the resulting image on the CRT display 51 and perform image enhancement functions using programs executed by the work station CPU 50.

Figure 4:
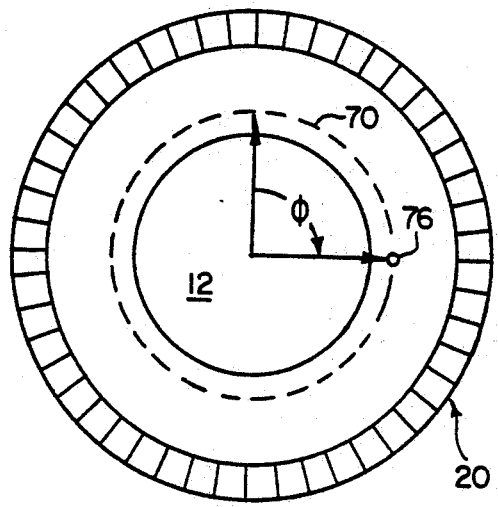
FIG. 4 is a schematic representation of the orbiting calibration source which forms part of the PET scanner system of FIG. 1.

When the PET scanner system is placed in the coincidence calibration timing mode it operates substantially different than its normal, imaging mode. As shown in FIG. 4, a reference source of positrons 76 is moved in circular orbit 70 in the bore 12 and coincidence events are detected by the front end electronics and registered by the coincidence detector 32. As described in the above-cited co-pending application Ser. No. 919,456, the coincidence data packet which is passed on to the sorter 34 includes not only the identity of the detector channels 20 which produce the event, but also the time difference information. For example, if the coincidence detector 32 recognizes a pair of events which occur within 6 nanoseconds of each other, a coincidence data packet will be produced for the sorter 34 which includes the 6 nanosecond time difference. As will be explained below, these time difference values are stored as a spectrum which has a peak that indicates the timing offset between pairs of detector channels 20.

Figure 5:
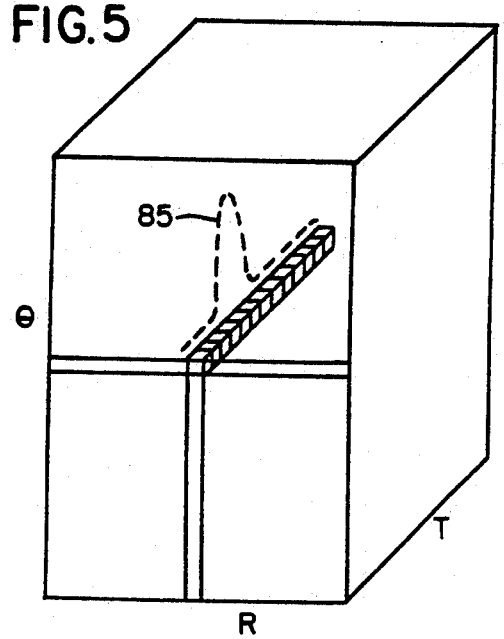
FIG. 5 is a graphic representation of a sinogram calibration array which is produced by the sorter which forms part of the PET scanner system of FIG. 2.

As described in co-pending U.S. patent application Ser. No. 920,350 filed on Jul. 27, 1992, and entitled "Sorter For Coincidence Timing Calibration In A PET Scanner," the sorter 34 employs the detector location information in the usual manner to produce an R,θ sinogram which indicates the number of coincidence events at each ray (R,θ). However, the time difference data (T) is also used by the sorter 34 to produce a third dimension on the sinogram. Such a three-dimensional calibration array is illustrated in FIG. 5, where the view angle (θ) and ray position (R) are two of the dimensions and the timing value (T) is the third dimension. The timing value may range from −31 to +32 nanoseconds. Each of the sixty four "bins" along this timing dimension (T) represents one of the possible measured time difference values, and each bin stores a total count of the number of coincidence events produced by the reference source along the ray θ,R with the particular time difference value. As a result, at the completion of the coincidence timing calibration acquisition, a histogram of the timing difference values have been collected for each ray (θ,R) as indicated by the dotted line 85. These histograms are employed to calibrate the acquisition circuits 25 in the gantry 10. The disclosure of this co-pending application Ser. No. 920,350 is incorporated herein by reference.

Referring particularly to FIG. 2, a three-dimensional calibration sinogram 48 is produced for each of the three rings of detectors 20 and the four cross rings and are stored in the memory 43. As will be described in more detail below, these three-dimensional calibration sinograms 48 are processed to produce a calibration file which contains a time delay value for each acquisition circuit 25 in the gantry 10. In response to a command from the workstation 15, this calibration file is downloaded to the acquisition CPU 29 through the serial link 18, which in turn downloads the separate delay time values through a serial link 55 to the corresponding acquisition circuits 25. As will be described below, each time delay value is imposed on the EDP pulse produced by the acquisition circuit 25. These corrections to the time delays in each acquisition circuit 25 are intended, of course, to equalize the time delays imposed on the EDP pulse by each front end channel of the PET scanner. In practice, it has been found that by repeating the timing calibration scan and downloading the resulting calibration file three or four times in succession, the timing errors are reduced to less than ±200 picoseconds. This entire process is automatic and is under the direction of a program executed by the workstation CPU 50. The operator initiates the calibration scan and allows the process to repeat until the values in the calibration file are small enough. The system is then switched out of the timing calibration mode and is ready for imaging.

Figure 6:
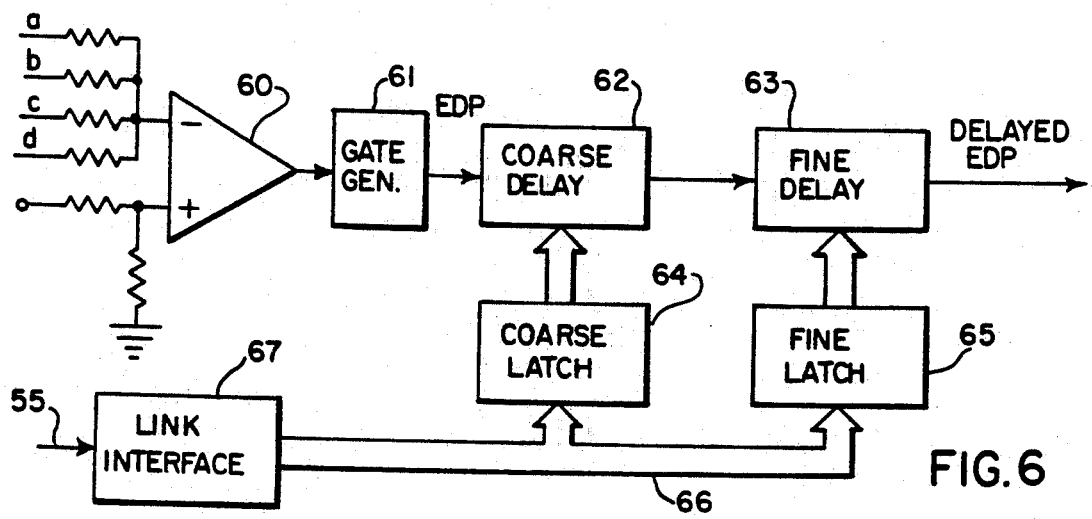
FIG. 6 is a schematic diagram of a part of a data acquisition circuit which forms part of the PET scanner system of FIG. 2.

Referring particularly to FIG. 6, each acquisition circuit 25 in the front end electronics of the PET scanner system includes a comparator 60 which receives and sums the four signals 23A-23D from its detector channel 20. When an annihilation event is detected, the comparator 60 produces a logic low signal at its output which enables a gate generator 61. The gate generator 61 produces an EDP pulse at its output which is employed by the system to determine exactly when the annihilation event occurred. It is the timing of this EDP pulse which is the subject of the present invention, and particularly, the delay of this EDP pulse such that the timing of all detector channels are the same.

The EDP pulse passes through two time delays 62 and 63 before being conveyed to the event locator 27. The delays 62 and 63 are each eight bits in length with the coarse delay 62 providing delay increments of 2 nanoseconds and the fine delay 63 providing delay increments of 200 picoseconds. The coarse delay 62 is set by an 8-bit value stored in a coarse latch 64 and the fine delay 63 is set by an 8-bit value in a fine latch 65. The values in the latches 64 and 65 are downloaded through the serial link 55 as part of the calibration file, and coupled to the latches 64 and 65 through bus 66 by a link interface 67. The total delay imposed on the EDP pulse is thus the sum of the delays provided by circuits 62 and 63 as determined by the 16-bit time delay value for this detector channel in the calibration file.

Referring particularly to FIGS. 7 and 8, the calibration file is produced under the direction of a program executed by the image CPU 42 at the completion of the calibration scan. In the preferred embodiment a pair of three-dimensional timing spectrum arrays 90 are produced by the sorter 34 for each of the three detector rings in the gantry 10. In addition, four pairs of three-dimensional timing spectrum arrays are produced for the cross ring timing values. As indicated by process block 91 in FIG. 7, the first step is to determine the peak time (T) of each histogram 85 in each of these fourteen timing spectrum arrays 90 and produce corresponding two-dimensional time difference arrays 92. The time difference arrays 92 store at each of their elements (R,θ) a floating point number which indicates the time difference between detected events along a particular ray R,θ. As indicated in the above-cited co-pending application Ser. No. 920,350, one of these time difference arrays 92 represents values acquired while the orbiting positron source 76 is to one side of the center, and the other timing array 92 in each pair represents values acquired while the source 76 is on the opposite side. As indicated by process block 93, the time-of-flight difference introduced into each of these timing arrays 92 is precisely eliminated by adding their corresponding values together to form a single two-dimensional time difference array 94. For example, a value of +3 nanoseconds at element R,θ in one array 92 is added to a value of −2 nanoseconds from the corresponding element R,θ in the other array 92 to produce the value +1 nanoseconds for the element R,θ in the two-dimensional time difference array 94.

Figure 9:
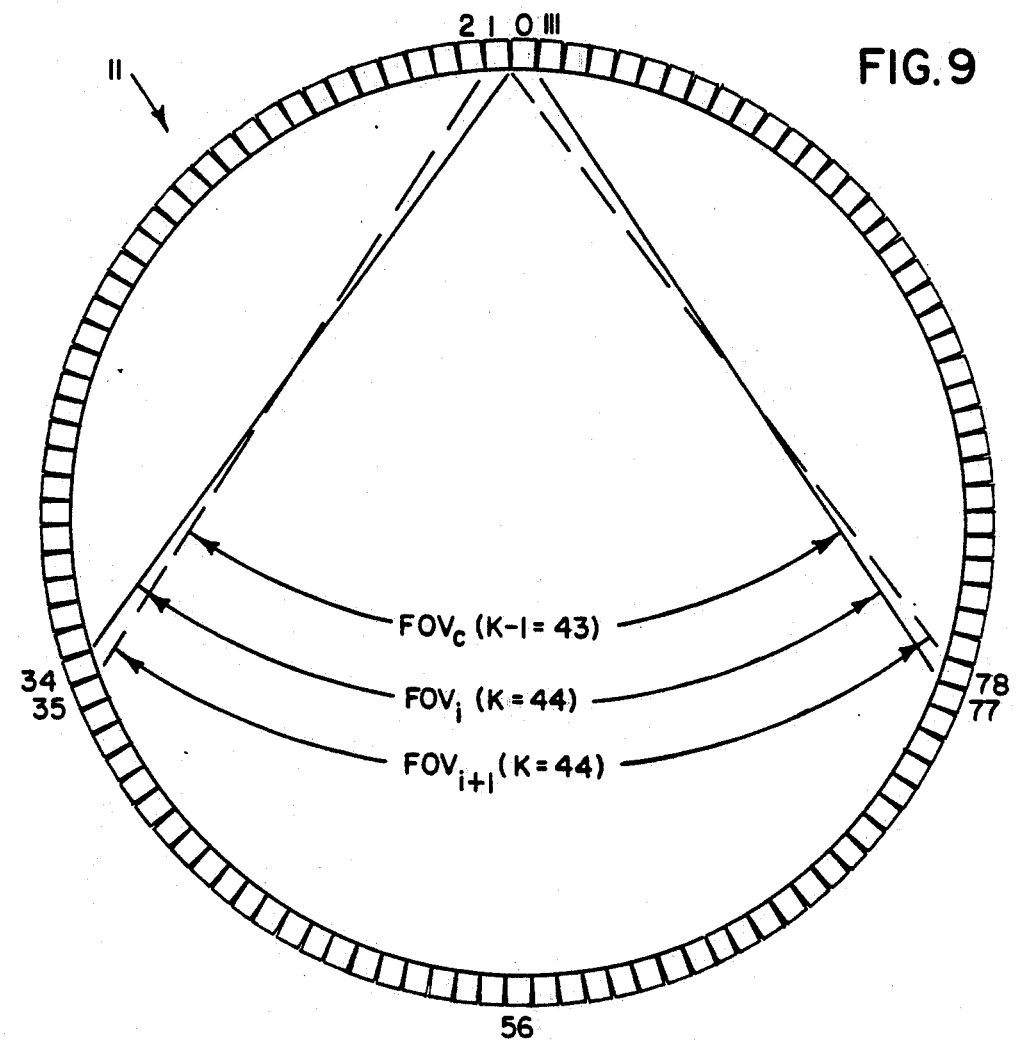
FIG. 9 is a schematic representation of one ring of detector channels which form part of the PET scanner system of FIG. 2.

Referring still to FIGS. 7 and 8, a loop is then entered in which a two-dimensional time difference array 94 for each of the three rings of detectors 20 is processed to form corresponding calibration files 95. As indicated by process block 96 a number of values and indices are initialized, including an index i which identifies the detector channel (0-111) being processed. As shown in FIG. 9, there are 112 separate detector channels to be processed, commencing with channel 0 located at the top of the detector ring 11 and working around the ring 11 in the counter clockwise direction until the detector channel 111 is processed. The resulting calibration file 95 is a set of 112 time delay values $\Delta \tau_i$ which indicate the adjustment required in the time delays of the corresponding data acquisition circuits 25.

Referring particularly to FIGS. 7 and 9, the time delay value $\Delta \tau_i$ for each detector channel (i) is calculated by averaging a set of the timing values in array 94. Specifically, the timing values selected are those for rays (R,θ) that lie within the field of view seen by both the detector channel i and the next detector channel i+1. As shown in FIG. 9, for example, the field of view (FOV$_i$) of channel i=0 includes k=44 rays which extend between channel i=0 and the channels ranging from channel 34 to 77. The next detector channel i=1 also has a field of view (FOV$_{i+1}$) which ranges over 44 rays and includes channels 35 to 78. Thus, the field of view common to both channels (FOV$_c$) includes 43 rays (k−1) ranging from channels 35 to 77. As indicated by process block 97, an incremental time delay value $\tau_i$ for the detector channel i is calculated by finding the average of the timing values in array 94 which correspond to the rays in the common field of view FOV$_c$:

$$\tau_i = \sum_{\phi=\phi_i}^{\phi=\phi_i+k-1} \frac{T_{i\phi}}{k-1} \quad (5)$$

where:
$\phi_i$=start of FOV$_c$ for detector channel i
$T_{i\phi}$=timing value in array 94 for the ray (R,$\theta$) between detector channel i and detector channel $\phi$.
For the initial detector channel (i=0) in the ring 11, this value is also the absolute time delay adjustment value $\Delta\tau_i$ used to update the delay setting stored in the calibration file 95. It is the reference value against which all other detector channels in the ring 11 will be calibrated.

For the remaining 111 detector channels in the ring 11 a reference correction $\Gamma$ is made to the incremental time delay value $\tau_i$ to produce the absolute time delay adjustment value $\Delta\tau_i$ for the calibration file 95:

$$\Delta\tau_i = \tau_i - \Gamma \quad (6)$$

This is indicated at process block 98. This is followed by the calculation of the reference correction $\Gamma$ for the next detector channel i+1 as indicated at process block 99. This is accomplished by first calculating the average of the timing values over the same common field of view FOV$_c$ as seen by the next detector channel i+1.

$$\tau_{i+1} = \sum_{\phi=\phi_i}^{\phi=\phi_i+k-1} \frac{T_{i+1,\phi}}{k-1} \quad (7)$$

where:
$T_{i+1,\phi}$=timing value in array 94 for the ray (R,$\theta$) between detector channel i+1 and detector channel $\phi$.
The reference correction $\Gamma$ is the difference between the average value as seen by the detector channel i and the average value as seen by the next detector channel i+1:

$$\Gamma = \tau_i - \tau_{i+1} \quad (8)$$

During the first pass through process block 99, $\Gamma$ is calculated using equations (7) and (8), but during subsequent passes it is changed by merely adding the timing value of the ray to detector channel $\phi=\phi_i+(K-1)$ and subtracting the timing value of the ray to detector channel $\phi=\phi_{i-1}$:

$$\Gamma_i = \Gamma_{i-1} + (T_{i+1,\phi i+(k-1)} - T_{i+1,\phi i-1})/(k-1) \quad (9)$$

The process thus continues around the detector ring 11 with an incremental time delay value $\tau_i$ being calculated for each detector channel i using equation (5) and an adjustment made to that value at process block 98 using the reference correction $\Gamma$ calculated during the previous iteration. When the entire ring 11 has been processed determined at decision block 100, there is no need to carry the calculation around the detector ring again because $\Gamma$ is by definition zero at this point.

The center detector ring is processed first, and before looping back to process other detector rings, a ring-to-ring reference adjustment value is calculated. This is accomplished at process block 101 by finding the average of the values in the time difference arrays 94 which store cross ring time difference data. That is, there are two cross ring arrays 94 having time difference values between the center ring and each of the outer rings. These values are averaged and this reference time difference value is added to the time delay adjustment values calculated for each detector channel in the outer ring. When the center ring and both outer detector rings have been processed as determined at decision block 102, the calibration files 95 for all three rings have been computed and are downloaded to the gantry 10 as indicated at process block 103. This calibration is extendable to any number of detector rings in the system as long as at least one coincidence line is shared between adjacent rings and this cross ring time difference data is captured by the sorter.

I claim:

1. In a PET scanner having a set of detectors located at successive locations around a ring and a corresponding set of detector channels which produce event data indicative of annihilation events occurring between pairs of detectors in the ring, a method for calibrating the coincidence timing of the detector channels which comprises:
    a) producing timing data which indicates the measured time differences of coincidence events occurring between each pair of detectors lying within the field of view of the PET scanner;
    b) calculating an incremental time delay $\tau_i$ for a detector in the ring by averaging the time difference values in the timing data which corresponds with pairs of detectors lying within the field of view of the PET scanner as seen from said detector;
    c) calculating a reference correction $\Gamma$ which relates the incremental time delay $\tau_i$ to the time delay calculated for a detector designated as the reference;
    d) combining the incremental time delay $\tau_i$ with the reference correction $\Gamma$ to produce the time delay adjustment value for the detector;
    e) repeating steps b) through d) for successive detectors in the ring until time delay values have been produced for all detectors in the ring; and
    f) downloading the time delay values to the corresponding detector channels to effect the timing thereof.

2. The method as recited in claim 1 in which calculation of the reference correction $\Gamma$ includes averaging the time difference values in the timing data which corresponds with pairs of detectors lying within the field of view of the PET scanner as seen from an adjacent detector in the ring.

3. The method as recited in claim 1 in which the timing data is stored in a sinogram array.

4. The method as recited in claim 1 in which there is a second ring of detectors, steps a) through e) are repeated for the second detector ring and the time delay values for the detectors in the second detector ring are adjusted to reference them to the timing values for the detectors in the first detector ring, and downloading the adjusted time delay values to the corresponding detector channels for the second detector ring.

5. The method as recited in claim 4 which includes producing cross-ring timing data which indicates the measured time differences of coincidence events occurring between pairs of detectors located in the two detector rings and lying within the field of view of the PET scanner, and the adjustment made to the time delay values for the second detector ring is determined using the cross-ring timing data.

6. The method as recited in claim 5 in which the adjustment made to the time delay adjustment values for the second detector ring is determined from the average value of the cross-ring timing data.

7. In a PET scanner having a set of detectors located at successive locations around a region of interest and a corresponding set of detector channels which produce event data indicative of annihilation events occurring between pairs of detectors, a method for calibrating the coincidence timing of the detector channels which comprises:

a) producing timing data which indicates the measured time differences of coincidence events occurring between each pair of detectors lying within the field of view of the PET scanner;

b) calculating an incremental time delay $\tau_i$ for a detector by averaging the time difference values in the timing data which corresponds with pairs of detectors lying within the field of view of the PET scanner as seen from said detector;

c) calculating a reference correction $\Gamma$ which relates the incremental time delay $\tau_i$ to the time delay calculated for a detector designated as the reference;

d) combining the incremental time delay $\tau_i$ with the reference correction $\Gamma$ to produce the time delay adjustment value for the detector;

e) repeating steps b) and d) for successive detectors in the set until time delay values have been produced for all detectors in the set; and f) downloading the time delay values to the corresponding detector channels to effect the timing thereof.

8. The method as recited in claim 7 in which calculation of the reference correction $\Gamma$ includes averaging the time difference values in the timing data which corresponds with pairs of detectors lying within the field of view of the PET scanner as seen from an adjacent detector in the ring.

* * * * *